US00PP16403P2

(12) United States Plant Patent
Austin

(10) Patent No.: US PP16,403 P2
(45) Date of Patent: Apr. 4, 2006

(54) SHRUB ROSE PLANT NAMED 'AUSBONNY'

(50) Latin Name: *Rosa hybrida*
Varietal Denomination: AUSbonny

(75) Inventor: David C. H. Austin, Albrighton (GB)

(73) Assignee: David Austin Roses Ltd., Albrighton (GB)

( * ) Notice: Subject to any disclaimer, the term of this patent is extended or adjusted under 35 U.S.C. 154(b) by 130 days.

(21) Appl. No.: 10/894,933

(22) Filed: Jul. 19, 2004

(51) Int. Cl.
*A01H 5/00* (2006.01)

(52) U.S. Cl. ..... Plt./102
(58) Field of Classification Search ..... Plt./102
See application file for complete search history.

*Primary Examiner*—Anne Marie Grunberg
*Assistant Examiner*—Annette H Para
(74) *Attorney, Agent, or Firm*—Klarquist Sparkman LLP

(57) ABSTRACT

Shrub rose plant having blush pink blooms, touched with apricot; rosette shaped flowers, distinctly quartered; free and continuous flowering; arching branches, providing a wide, mounding shrub; and pleasing fruity fragrance.

1 Drawing Sheet

Figure 1:
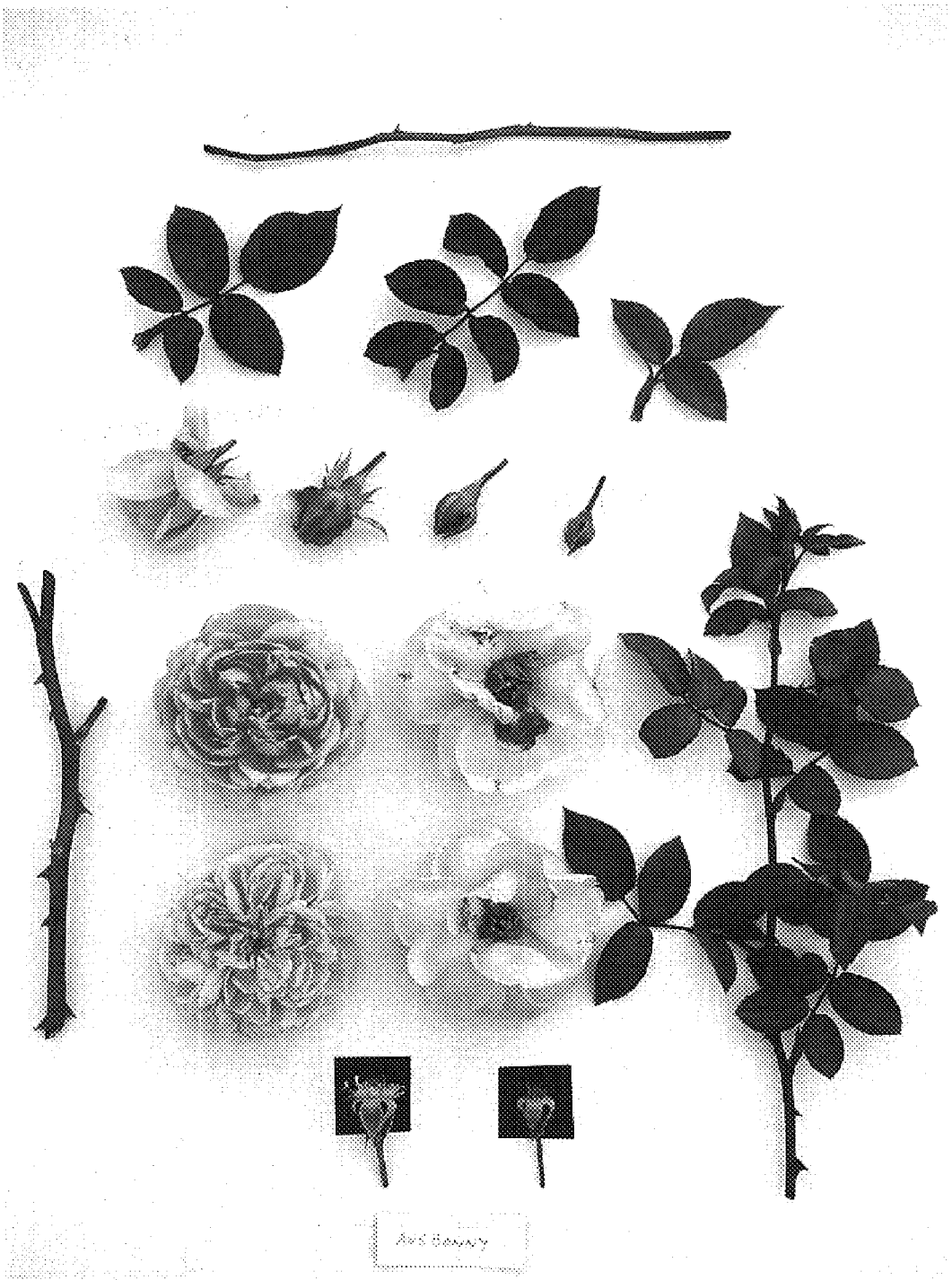

Genus and species: *Rosa hybrida.*
Variety denomination: 'AUSbonny'.

ORIGIN OF THE INVENTION

The present invention relates to a new and distinct variety of a shrub rose plant named 'AUSbonny' which was originated by me by crossing an unnamed seedling (not patented), with the variety 'AUSgold' (Golden Celebration), (U.S. Plant Pat. No. 8,688).

BACKGROUND OF THE INVENTION

The primary objective of this breeding was to produce a new rose variety being very robust and healthy, very free flowering, having blush pink blooms touched with apricot, and a pleasing fruity fragrance.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Blush pink blooms, touched with apricot;
2. Rosette shaped flowers, distinctly quartered;
3. Free and continuous flowering;
4. Arching branches, providing a wide, mounding shrub;
5. Pleasing fruity fragrance.

Asexual reproduction of this new variety by budding, as performed at Albrighton, England, shows that the foregoing and all other characteristics and distinctions come true to form and are established and transmitted through succeeding propagations.

Comparison with Parents

The subject variety differs from its male parent 'AUSgold' (Golden Celebration) in flower color (golden-yellow for 'AUSgold', blush pink for 'AUSbonny'), and the large, cupped size of flowers of 'AUSgold' compared to the medium sized flowers of 'AUSbonny'.

Comparison with Similar Variety

The closest variety known to me is 'AUSecret', U.S. Plant patent application Ser. No. 09/947,252, filed Sep. 5, 2001 for which has soft pink blooms with greater petalage than the blush pink blooms of 'AUSbonny'.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (2001), except where ordinary dictionary significance of color is indicated.

Parentage:
*Seed parent.*—Unnamed Seedling. Not patented.
*Pollen parent.*—'AUSgold' (Golden Celebration). U.S. Plant Pat. No. 8,688.

FLOWER

Observations made in August 2003 from one year old bare root plants, grown in a garden environment at Albrighton, England.

Blooming habit: Recurrent.
Bud:
*Size.*—About 3 cm long and 1.6 cm in diameter when the petals start to unfurl.
*Form.*—The bud form is pointed ovoid.
*Color.*—When sepals first divide, bud color is Yellow-Green Group 144B. When half blown, the upper sides of the petals on the outer two thirds are Red Group 56A; the lower sides of the petals are Red Group 56D.

*Sepals*.—Color: Upper surface: Yellow-Green Group 146C, Lower surface: Yellow-Green Group 146D. Length: 1.8 cm. Width: 1 cm. Shape: Pointed. Surface texture: Upper surface: Slightly hairy. Lower surface: Smooth. There are three lightly appendaged sepals. There are two unappendaged sepals with hairy edges.

*Receptacles*.—Color: Yellow-Green Group 144A. Shape: Funnel. Size: About 2 cm long×1.6 cm wide. Surface: Smooth.

*Peduncle*.—Length: Medium, averaging about 4.5 cm. Surface: Smooth. Color: Yellow-Green Group 144B. Strength: Erect.

Bloom:

*Size*.—Medium. Average open diameter is about 7.5 cm.

*Borne*.—In rounded clusters of about four blooms.

*Stems*.—Strength: Normal. Average length is about 8.5 cm with a diameter of 0.8 cm.

*Form*.—When first open: Flat, high centered. Permanence: Retains its form to the end, outer petal edges curl back.

*Petalage*.—Number of petals under normal conditions: 70.

*Color*.—The upper sides of the petals are Red Group 36D at the outer part and Red Group 36B toward the base. The reverse sides of the petals are Red Group 36D. The base of each petal is Yellow Group 3C. The major color on the upper side is Red Group 36D.

*Variegations*.—None.

*Discoloration*.—The general tonality at the end of the first day: Orange Group 29B. At the end of the third day: Fading to Red Group 36B.

*Fragrance*.—Moderate, fruity.

Petals:

*Texture*.—Thick, satiny.

*Size*.—Width: 2.8 cm. Length: 3.6 cm.

*Shape*.—Round, notched.

*Surface*.—Smooth.

*Margin*.—Reflexing and undulating.

*Apex shape*.—Round.

*Base shape*.—Pointed.

*Form*.—Tips slightly recurved and moderately quilled.

*Arrangement*.—Quartered.

*Petaloids*. Number: 4. Color: Red Group 37C.

*Persistence*.—Petals hang on and dry.

*Lastingness*.—On the plant: Long (about 6 days). As a cut flower: Fair (about 4 days).

Reproductive parts:

*Stamens*.—Number: 37. Length: 4 mm. Anthers: Length: 2 mm. Color: Yellow-Orange Group 21A. Arrangement: Mixed with petaloids. Filaments: Color: Yellow-Orange Group 19A. Length: 3 mm. Pollen: Color: Yellow-Orange Group 21A.

*Pistils*.—Number: 45. Length: 5 mm. Styles: Color: Yellow Group 10B. Length: 5 mm. Stigmas: Color: Yellow Group 10B. Length: 3 mm.

*Hips*.—None observed.

PLANT

*Form*.—Shrub.

*Growth*.—Medium, branching.

*Age at maturity*.—2 years.

*Mature plant*.—Height: 1 m. Width: 75 cm.

*Rootstock*.—Dr. Huey in the USA. Rosa Dumetorum Laxa for the observed plants in the UK.

Foliage: Number of leaflets on normal mid-stem leaves: 5.

*Size*.—Medium. About 12 cm long×8.5 cm wide.

*Quantity*.—Normal.

*Color*.—New foliage: Upper and lower sides: Yellow-Green Group 146A with a margin and mid-rib of Greyed-Orange Group 176B. Lower side: Yellow-Green Group 146C with a margin and mid-rib of Greyed-Orange Group 176B. Old foliage: Upper side: Yellow-Green Group 147A. Lower side: Yellow-Green Group 146B.

Leaflets:

*Size*.—About 4.5 cm long×2.8 cm wide.

*Shape*.—Pointed oval.

*Base shape*.—Obtuse.

*Apex shape*.—Acuminate.

*Texture*.—Leathery.

*Edge*.—Serrated.

*Serrations*.—Large.

*Petiole*.—Color: Yellow-Green Group 144B.

*Petiole rachis*.—Color: Yellow-Green Group 144B. Underside: With prickles.

*Auricle shape*.—Pointed.

*Stipules*.—Length: 2.5 cm, bearded.

*Disease resistance*.—Resistant to mildew, rust and blackspot under normal growing conditions.

*Pest resistance*.—Not tested.

*Vein color*.—Yellow-Green Group 146B.

*Venation pattern*.—Net-veined.

Wood:

*New wood*.—Color: Green Group 143B with blush of Greyed-Orange Group 176B. Bark: Smooth.

*Old wood*.—Color: Yellow-Green Group 144A with blush of Greyed-Orange Group 176A. Bark: Smooth.

Prickles:

*Quantity*.—On main canes from base: Few. Number per stem length: 16 per 30 cm. On laterals from main canes: Few. Number per stem length: 6 per 30 cm.

*Form*.—Hooked downward.

*Length*.—35 mm.

*Color when young*.—Yellow-Green Group 143B with blush of Greyed-Orange Group 176B.

*Color when mature*.—Yellow-Green Group 144A with blush of Greyed-Orange Group 176B.

Small prickles:

*Quantity*.—On main stalks: Few. On laterals: Few.

*Color*.—When young: Red Group 42C. When mature: Greyed-Red Group 178B.

Winter hardiness: Not tested.

I claim:

1. A new and distinct variety of rose plant of the shrub class, substantially as herein shown and described, characterized particularly by its blush pink blooms, touched with apricot; rosette shaped flowers, distinctly quartered; free and continuous flowering; arching branches, providing a wide, mounding shrub; and pleasing fruity fragrance.

* * * * *